United States Patent
Takemoto

(10) Patent No.: US 6,264,468 B1
(45) Date of Patent: Jul. 24, 2001

(54) ORTHODONTIC APPLIANCE

(76) Inventor: Kyoto Takemoto, 3-89-3, Shinmatsudo, Matsudo-shi, Chiba 270-0034 (JP)

( * ) Notice: Subject to any disclaimer, the term of this patent is extended or adjusted under 35 U.S.C. 154(b) by 0 days.

(21) Appl. No.: 09/402,905

(22) PCT Filed: Feb. 19, 1999

(86) PCT No.: PCT/JP99/00750
§ 371 Date: Oct. 12, 1999
§ 102(e) Date: Oct. 12, 1999

(87) PCT Pub. No.: WO99/42056
PCT Pub. Date: Aug. 26, 1999

(30) Foreign Application Priority Data

Feb. 19, 1998 (JP) .................................................. 10-037669

(51) Int. Cl.⁷ .................................................. A61C 3/00
(52) U.S. Cl. .................................. 433/8; 433/10; 433/20
(58) Field of Search ................... 433/8, 9, 10, 16, 433/20, 22, 24

(56) References Cited

U.S. PATENT DOCUMENTS

| | | | |
|---|---|---|---|
| 4,337,037 | 6/1982 | Kerz | 433/8 |
| 4,386,908 | 6/1983 | Kurz | 433/9 |
| 4,443,189 | * 4/1984 | Wildman | 433/10 |
| 4,496,317 | * 1/1985 | Hulsey | 433/10 |
| 4,669,980 | 6/1987 | Degnan | 433/8 |
| 4,669,981 | 6/1987 | Kurz | 433/9 |
| 4,698,017 | 10/1987 | Hanson | 433/11 |
| 4,909,735 | * 3/1990 | Wildman | 433/24 |
| 5,516,284 | 5/1996 | Wildman | 433/10 |
| 5,711,666 | 1/1998 | Hanson | 433/11 |
| 5,791,897 | 8/1998 | Wildman | 433/10 |
| 5,863,199 | 1/1999 | Wildman | 433/10 |

FOREIGN PATENT DOCUMENTS

| | | |
|---|---|---|
| 53-78699 | 7/1978 | (JP) . |
| 57-44967 | 10/1982 | (JP) . |
| 1-41332 | 9/1989 | (JP) . |
| 5-154166 | 6/1993 | (JP) . |

* cited by examiner

Primary Examiner—Gene Mancene
Assistant Examiner—Melba Bumgarner
(74) Attorney, Agent, or Firm—Merchant & Gould P.C.

(57) ABSTRACT

When an orthodontic appliance is attached to the lingual side (back side) of teeth which is invisible from the outside, a large difference in level of the surface between adjacent teeth requires utilization of a wire bent in a complicated fashion. It has been found, however, that the difference in level between adjacent teeth is very small in a horizontal plane at a boundary between a crown and a root, thereby making it possible to draw a smooth envelope therealong. Based on this finding, with a view to placing a wire along such an envelope, a "lingual straight archwire" having a planar configuration comprising a simple curve and straight lines smoothly connected to ends of the curve and residing in a single horizontal plane and a bracket having a configuration suitable for the placement of the archwire are provided.

8 Claims, 15 Drawing Sheets

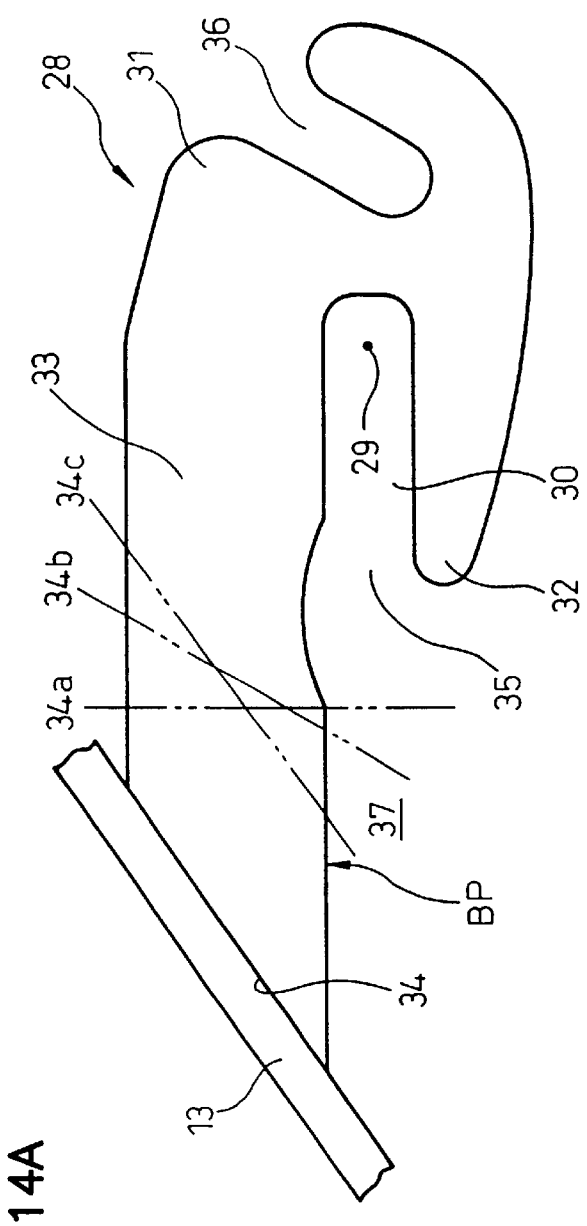
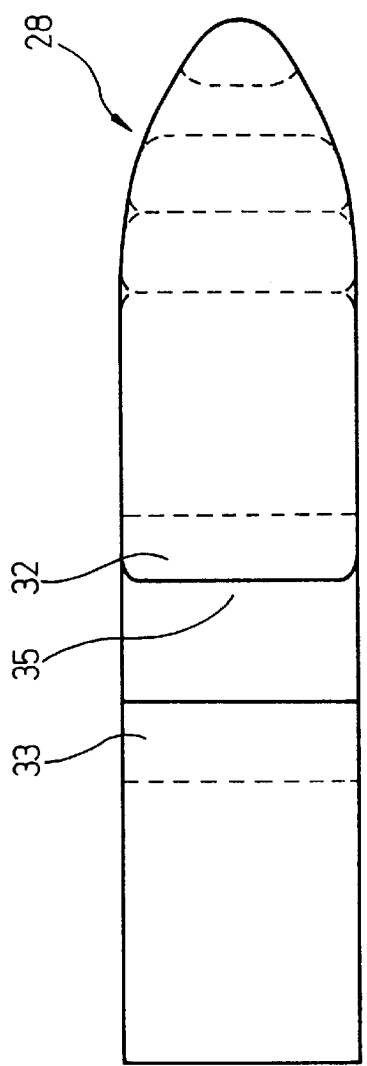
FIG. 14A
FIG. 14B

| | A | B | C |
|---|---|---|---|
| 1 | 6.3 | 0.0 | 6.3 |
| 2 | 5.3 | 1.2 | 6.5 |
| 3 | 5.2 | 1.3 | 6.5 |
| 5 | 5.8 | 0.8 | 6.6 |
| 6 | 7.1 | 0.5 | 7.6 |
| 7 | 6.8 | 0.5 | 7.3 |

(mm)

|   | A | B | C |
|---|---|---|---|
| 1 | 5.2 | 0.0 | 5.2 |
| 2 | 5.3 | 0.3 | 5.6 |
| 3 | 5.3 | 0.7 | 6.0 |
| 5 | 6.0 | 0.5 | 6.5 |
| 6 | 7.4 | 0.5 | 7.9 |
| 7 | 7.4 | 0.5 | 7.9 |

(mm)

| | A | B | C |
|---|---|---|---|
| 1 | 5.1 | 0.0 | 5.1 |
| 2 | 5.2 | 0.2 | 5.4 |
| 3 | 5.2 | 0.5 | 5.7 |
| 4 | 5.6 | 0.5 | 6.1 |
| 5 | 6.0 | 1.0 | 7.0 |
| 6 | 7.4 | 0.5 | 7.9 |
| 7 | 7.4 | 0.5 | 7.9 |

(mm)

ORTHODONTIC APPLIANCE

FIELD OF THE INVENTION

The present invention relates to an orthodontic appliance for use for orthodontics, in which an improper alignment of teeth is corrected, the appliance including a wire and brackets adapted to be affixed to a tooth so that the wire can be hooked thereon.

PRIOR ART

Almost every conventional orthodontic appliance including a wire and brackets for correcting an improper alignment of teeth is adapted to be attached to an external side, i.e., a "labial side" of a tooth. The reason for such attachment is because the brackets and wire are easily attached to the labial side of a tooth and because the wire is easily adjusted on the labial side, when needed, as the correction progresses. In a case where an orthodontic appliance is attached to the labial side of teeth, however, every time the patient opens his or her mouth, the metallic orthodontic appliance, which looks abnormal at a glance, can be seen by other people, and therefore wearing such an orthodontic appliance for a long treatment period of nearly two years gives the patient under treatment a considerable amount of mental anguish.

To solve this problem and relieve such anguish an orthodontic appliance has been developed in which wires and brackets are attached to the internal side, i.e., the "lingual side" of teeth, where they are difficult to see from the outside, and such an orthodontic appliance has been used by some orthodontists, in actual orthodontic practice, for a long time. Japanese Examined Patent Publication (Kokoku) No. 57-44967 and the specification of U.S. Pat. No. 4,337,037 describe examples of such conventional orthodontic appliances that are attached to the lingual side of teeth. Brackets constituting a main component of such an orthodontic appliance are attached to the lingual surface of teeth using a bonding method or the like, and a common wire, the other main constituent component of the appliance, is then hooked in slots formed in the brackets. Thereafter, the common wire is ligated to the slots of the respective brackets with separate thin wires or the like. In general, the conventional brackets and wire that are affixed to the lingual surface of teeth have configurations illustrated in FIGS. 2 and 3, and FIGS. 4 and 5, and most of the parts thereof are made of metal (alloy).

A bracket 10 used in a first example of a conventional orthodontic appliance comprises, as shown in FIG. 2, a plate-like pad 13 adapted to be bonded to a surface 12 of a tooth 11 on the lingual (internal) side thereof and a bracket main body 14 made integral with the pad 13 by brazing or the like in such a manner as to be erect from the lingual surface of the pad 13. The bracket main body 14 has three finger-like portions, which permits a main slot 15 and a sub-slot to be formed in the bracket 10, the main slot 15 opening perpendicularly downward (when affixed to the maxilla) or perpendicularly upward (when affixed to the mandible) in a state in which the bracket 10 is affixed to the lingual surface of a tooth and the sub-slot 16 opening horizontally towards the lingua (in the above bracket affixing situation), and a wire 17 which is constituted by a metallic wire of an alloy or the like and has, for instance, a square cross-section is inserted into either of the slots 15, 16. The wire 17 generates, from a bending force or tension as a restoring force resulting from its intrinsic elasticity, a corrective force or moment to be imparted to a tooth or teeth 11 which deviate from a proper dental arch or are improperly rotated and moves or rotates the respective improperly positioned teeth 11 to proper positions on the dental arch, over time.

Furthermore, slots 18 and 19 between upper and lower portions of the bracket main body 14 and the pad 13 are used such that for instance, a thin wire or rubber band is hooked therein so as to ligate the wire 17 inserted into the main slot 15 (or the sub-slot 16) to the bracket 10 for fixation thereto. In addition, reference numerals 20, 21 denote a position of a central point or center line of the wire 17 when the wire 17 is installed in either of the slots 15, 16.

FIG. 3 shows a second example of a conventional orthodontic appliance that is affixed to the lingual side of a tooth. A bracket 22 in the second example has a pad 13 similar to that used with the bracket 10 in the first example of the conventional appliance, as shown in FIG. 2, and formed in a bracket main body 23, that is made integral therewith, is a main slot 24 which opens horizontally towards the lingua. In addition, as in the case shown in FIG. 2, upper and lower slots 18 and 19 are also formed between the bracket main body 23 and the pad 13, and at least one of the two can be used such that a thin wire or the like is hooked therein so as to ligate thereto a wire 17 when the wire 17 is inserted into a predetermined position in the main slot 24 indicated by reference numeral 25 denoting a central point (line) of the wire.

FIG. 4 is a plan view of all the mandibular teeth when the conventional bracket 10 shown in FIG. 2 is affixed to the lingual surface of the respective teeth 1 to 7 represented by the anterior teeth 11. In a case where the teeth are in a normal alignment, as is clear from FIG. 4, the surfaces on the labial side (outside) of the respective teeth 1 to 7 are in alignment with one another along the row of teeth without large irregularities in the surfaces and since, in many cases, there can be contemplated a smooth envelope relative to the labial surfaces of the respective teeth, as has been done conventionally, in a case where an orthodontic appliance comprising a wire and brackets is affixed to the labial side of a tooth, it is possible to use as a wire a smoothly curved "straight" wire which is free of specific bent portions (points where there is a drastic change in direction). On the other hand, there are marked irregularities in the lingual surfaces of a row of teeth when viewed in a vertical direction, and therefore in general there can be contemplated no smooth envelope relative to the lingual surfaces of the respective teeth.

Even in a normal condition, anterior teeth such as a central incisor 1, a lateral incisor 2 and a canine tooth 3 are inclined, slightly curved and pointed, and have a relatively elongated vertical section as is clear from a tooth 11 shown in FIGS. 2 and 3. Moreover, although they look like as if they are scooped out on the lingual side in the crown, as is clear from FIG. 4, they are even with one another on the lingual surfaces in terms of teeth alignment. It is common, however, that there is a relatively large difference in the level of the lingual surface between the canine tooth 3 of the anterior teeth and a first premolar 4 situated adjacent to the canine tooth 3 and having a crown of a substantially cylindrical configuration in conjunction with a change in cross-sectional configuration between the anterior teeth and the posterior teeth. In addition, although the first premolar 4 and a second premolar 5 are generally in alignment with each other on the lingual side surface and a first molar 6 and a second molar 7 are also generally in alignment with each other on the lingual side surface, as is shown in FIG. 4, there is a slight difference in the level of the lingual side surface between the second premolar 5 and the first molar 6.

Consequently, a bracket 10, 22 is bonded to the lingual surface of the respective teeth 1 to 7 at a position as close to the gingiva 26 as possible, and where a pad 13 can be bonded, and a common wire 17 is then hooked in a main slot 15, 24 such that tips of the anterior teeth on the mandible do not come into contact with the bracket and wire, so mounted on the lingual surface of anterior teeth of the maxilla so as not to hinder occlusion between the maxilla and mandible. With this construction, even in a state in which the respective teeth 1 to 7 are all corrected to be at a normal position, the wire 17 at least has to be formed into a mushroom shape when viewed from the top in a vertical direction, having therealong many bent portions (b) as shown in FIG. 5. Therefore, in order to form a wire 17 into a mushroom configuration as shown in FIG. 5 in advance, a strong bending force is locally applied to a straight wire at positions where a bent portion (b) needs to be formed so as to produce a plastic deformation thereat, whereby four (refer to FIG. 5 and a dotted configuration shown in FIG. 7) or six (refer to a dotted configuration in FIG. 8) crank-shaped bent portions are formed along the wire, and then the wire so formed is inserted into slots in the brackets bonded to the respective teeth 1 to 7 for ligature. Thus, a complicated and troublesome process has been adopted. A wire 17 shaped as described above is referred to as a "mushroom-shaped archwire" among orthodontists due to the plan view thereof.

However, even when a mushroom-shaped archwire 17 is used, preparation of a wire formed into a mushroom shape as viewed from the top, as shown in FIG. 4 or 5, is not always sufficient. This is because, in many cases, there is a slight difference in the vertical level between main slots in brackets attached to adjacent teeth. Conventionally, no certain standardized positional relationship between the slots in the adjacent brackets has been taken into consideration when a bracket is bonded to the lingual surface of each tooth, and whether or not there is caused such a difference in level between slots in adjacent brackets largely depends on the configuration of a bracket used. Thus, since the heights of slots in adjacent brackets are also not the same in many cases, in order to cope with a difference in the vertical levels, i.e., a difference in height, it is general practice to form bent portions (b) not only in a horizontal direction but also in a vertical direction in a conventionally used mushroom-shaped archwire 17 in advance as shown in FIG. 6, thus making an archwire 17 a solid body bent in a three-dimensionally complicated fashion.

Conventionally, even for an orthodontic appliance adapted to be attached to the lingual side of a tooth, the configuration of a bracket is taken into consideration and a bracket is attached to a position on the lingual surface of a tooth which facilitates attachment, and moreover, a wire is hooked on the bracket at a position as close to the lingual surface of the tooth as possible. In addition, complicated crank portions are provided along an archwire by forming bent portions therealong in order to cope with the difference in level and height produced between adjacent teeth due to the differences in level of the lingual surfaces between adjacent teeth. Thus, conventionally there has been no other way but to use a mushroom-shaped archwire 17 as shown in FIG. 5.

In a case where a mushroom-shaped archwire having crank-shaped bent portions is used, a complicated special wire must be prepared in which bent portions are formed in accordance with the teeth alignment of each patient. In addition, an archwire must slide relative to a bracket as the corrective treatment progresses or as teeth under corrective treatment change their positions or rotate, and when they are so arranged, the bent portions formed along the wire never fail to interfere with the brackets, and this prevents smooth sliding of the wire. To cope with this, every time it must slide, the wire has to be re-bent (to be plastically reformed) so as to change the positions of the bent portions before it can slide for adjustment. Thus, an operation like this is very troublesome to the orthodontic operator, and the treatment time gets longer in proportion to the trouble, and requires the person to be treated to be very patient.

DISCLOSURE OF THE INVENTION

With a view to solving the aforesaid problem inherent in the prior art, it is an object of the present invention to provide a novel orthodontic appliance constituted mainly by a straight arch-like wire which is smoothly curved with no sharp bent portion formed therealong and requires no additional bending through plastic deformation (this wire being termed as "Lingual Straight Archwire and hereinafter, abbreviated as "LSW"). It is also an object of the present invention to provide a bracket, adapted to be attached to the lingual side of a tooth as part of an orthodontic appliance, having a configuration and a construction which are different from those of a conventional bracket and suitable for use with the aforesaid LSW.

The present invention provides orthodontic appliances, as set forth in the respective claims, as means for attaining the above objects.

Next, of history the orthodontic appliances described herein, as the means for solving the aforesaid problems, will be given. As described before, the prior art orthodontic appliance entails a problem in that troublesome operation work is needed for an orthodontic treatment which includes preparation of a mushroom-shaped archwire 17 having crank-shaped bent portions (b) provided by plastically deforming in advance the archwire in conformity with a difference in level of the lingual surface between adjacent teeth of each patient and re-bending the archwire so formed so as to change the position of the bent portions as the orthodontic treatment progresses. To cope with the problem, and with the view to replacing this prior art mushroom-shaped archwire 17 with an archwire comprising a smooth curve, which is substantially an arc, and linear portions following the curve from ends thereof without any difference in level, the archwire shown as the aforesaid LSW by solid lines in FIGS. 7 and 8, the inventor of the present invention prepared a number of models, each representing a state in which the maxilla and mandible which are received an orthodontic treatment are properly occluded in parallel, and then carried out in-depth investigations and studies using the models as samples.

First of all, the inventor compared a number of dental arch models with respect to the buccolingual diameter at the root surface of adjacent teeth. Here, the buccolingual diameter means the width (thickness between the front and back) of a tooth measured in a buccolingual direction at a cross-section in a horizontal plane considered as a boundary between a crown of each tooth exposed from a gingiva and a root thereof embedded in the gingiva. As a result of such comparison, it was found that with each dental arch model, there was only a slight difference in buccolingual diameter between two adjacent teeth, and as described before, even between the canine tooth 3 and the first premolar tooth 4 where normally there is provided a large difference in level of the lingual surface therebetween, the difference in buccolingual diameter was just smaller or larger than 1 mm, and the differences in buccolingual diameter found between any other two adjacent teeth was smaller than 1 mm.

This is because, when observing only the configuration of the crown of the anterior teeth, as shown in FIGS. 1 to 3, the crown is shaped such that it is largely scooped out in the lingual surface thereof, while, with the back teeth such as premolars and molars, the crown is in an hourglass or cylindrical shape, and therefore when observing the lingual surfaces of the canine tooth 3 and the first premolar 4 which provide therebetween a boundary between the anterior and posterior teeth, there is a large difference in level at the lingual surface. On the other hand, however, there is not much difference in level at the neck as a transition portion from the crown to the root. This is because both the anterior and posterior teeth have similarly a substantially circular cross-section at the neck thereof. As a result of the comparisons, the inventor came to a conclusion that a smooth envelope could be drawn even on the lingual side of teeth along a contour formed at the boundary between the crown and the root of the respective teeth against the conventional thinking that there can be drawn no smooth envelope on the lingual surface between the anterior teeth and premolars where a large difference in level is believed to exist.

As a result of further continued investigation and studies, the inventor found that, assuming that there are certain points on the lingual side of the respective teeth exhibiting a shared specific characteristic when viewed in a vertical direction, those points are arranged on a single shared smooth imaginary curve.

Here, the "points exhibiting a shared specific characteristic" means an apex of an expanded portion at the crown on the lingual surface of each tooth which protrudes toward the lingual side. Then, this point is termed as "Lingual Point" and abbreviated as "LP." This LP denotes an apex of a maximum protruding portion on the lingual side as shown in FIGS. 9(a) and (b) when talking about the back teeth such as those from the first premolar 4 to a second molar 7 while, when talking about the anterior teeth represented by a central incisor tooth, a lateral incisor tooth and the canine tooth 3, the LP denotes a most protruding point of a protruding portion on the lingual surface of the neck thereof as shown in FIG. 9(c).

Then, it was found that, when looking individually at the maxillary or mandibular teeth which have received an orthodontic treatment, the LP's (lingual point) of the respective teeth are, in general, arranged substantially systematically on a shared smooth curve. Additionally, an Embrasure Line by Andrews (abbreviated as "EL"), which extends continuously along contact points between adjacent teeth, was assumed, and a distance A between EL and LP was compared between any adjacent teeth. This disclosed a fact that a substantially identical distance A was measured between any adjacent teeth, and that with a largest difference in measured value being just over 1 mm, a difference of equal to or smaller than 1 mm was measured between almost all adjacent teeth.

In addition, as shown in FIG. 9, it was also found that the LP (lingual point) of each tooth resides on an imaginary horizontal plane that can be considered common to the maxilla and mandible, respectively. Therefore, it was made clear that the LP's of the maxillary or mandibular teeth are arranged on a smooth envelope drawn on a shared imaginary horizontal plane such as described above and that the LP constitutes a point of contact to a smooth envelope imagined relative to all the teeth on the maxilla and mandible, respectively.

Based on this knowledge, the inventor imagined another horizontal plane spaced away a distance substantially sufficient for insertion of a part of an orthodontic appliance including a bracket from the aforesaid imaginary horizontal plane containing an envelope formed as contacting the LP of each tooth on the maxilla and mandible, respectively, and termed this plane as "Lingual Straight Plane" (hereinafter, abbreviated as "LSP").

The inventor contrived a new orthodontic method comprising the steps of setting for the maxilla and mandible, respectively, a final target position at completion of a series of orthodontic treatment of an LSW (lingual straight archwire) 27 having a configuration comprising, as shown by solid lines in FIG. 7 or FIG. 8, a simple curve and straight lines on an LSP (lingual straight plane) set as described above in such a manner that the final target positions extend not only along the aforesaid envelope passing through the LP of every tooth of the maxilla and mandible, respectively, but also as close to the envelope as possible, using a bracket having a configuration and an arm length which are optimum for connecting the lingual surface of each tooth with the LSW 27 so that a slot in the bracket when attached to each tooth at completion of a series of orthodontic treatments coincides with the position of the LSW 27 so set, bonding a pad for the bracket to the lingual side of a tooth, hooking the LSW 27 in the slot of the bracket by deflecting a part of the LSW 27 corresponding to the slot within its elastic limit in accordance with the position and rotated state of each tooth, and ligating the LSW 27 to the slot of the bracket with a thin wire or rubber band in a conventional fashion. Therefore, the present invention provides an orthodontic appliance comprising an LSW 27 for use with the method and a bracket suitable for use with the LSW.

With a view to providing a means for clinically easily determining a vertical position of the above LSP (lingual straight plane) set for the LSW (lingual straight archwire) 27, the inventor concluded, after having studied a number of dental arch models, that it was reasonable to form the LSP as a horizontal plane extending toward the anterior teeth passing through a position each premolar or molar (back teeth) which is spaced away from the gingiva a distance equal to one half the height of the crown on the lingual side of each premolar or molar (back teeth) with either the maxilla or the mandible, as shown in FIGS. 9(a) and (b).

In the case of the maxilla, it was confirmed, from the studies of a number of dental arch models, that the LSP (lingual straight plane), which is determined as described above, should pass through a position, as shown in FIG. 9(c), spaced away from the gingiva a distance equal to one third the height of the crown on the lingual side of the anterior teeth, and in the case with the mandible, as with the premolars or molars, it was similarly confirmed that the LSP should pass through a position, as also shown in FIG. 9(c), spaced away from the gingiva a distance equal to one half the height of the crown on the lingual side of the anterior teeth.

Thus, although it is formed into a smooth and straight curve without any bent portions, the LSW (lingual straight archwire) of the present invention can apply a needed corrective force or moment to a tooth needing a correction by being inserted into a main slot of a bracket attached to the lingual surface of the tooth while bending the wire within its elastic deformation range (ultra-elastic deformation range when a shape memory alloy is used for the archwire) and ligating the inserted portion of the LSW 27 to the slot in the bracket attached to each tooth with a thin wire or rubber band.

In addition, since there is no need to form, on the LSW 27, a bent portion (b) which is plastically deformed in advance, as the orthodontic treatment progresses, even when the positional relationship between the bracket and the LSW 27 has to be adjusted, the LSW 27 may simply be caused to slide relative to the bracket, and since there is formed no bent portion (b) on the LSW 27, there is no risk of the LSW 28 being brought into collision with the slot with the bracket, and since this allows the LSW 27 to easily slide relative to the slot in the bracket at the ligated portion, the adjustment of the LSW 27, which is required as the orthodontic treatment progresses, can markedly be facilitated.

Next, in the orthodontic appliance according to the present invention, the bracket, which is optimum for connecting the LSW 27 to the lingual surface of a tooth, is indicated as 28 in FIG. 1. The bracket so constructed has the following features:

(1) Since the bracket 28 of the present invention has a main slot 30 formed in a horizontal direction for receiving the LSW 27 at a center point (line) thereof for ligature and a bracket main body 31 functioning to allow the slot to open toward a lingual surface 12 of a tooth 11, orthodontic work can easily be performed which includes installation of the LSW 27 into the main slot 30 and sliding adjustment of the LSW 27.

(2) The bracket main body 31 is provided with a leg portion 32 in order to construct the main slot 31 as described (1) above, but since there is formed a large space between the tip of the leg portion and a pad 13, when the bracket 28 is attached to the anterior tooth 11 of the maxilla as shown in FIG. 1, a bite plane BP facing the tip of an anterior tooth on the mandible is formed under a lower surface of an arm portion 33 of the bracket main body 31. Thus, the position of the BP is deepened with the bracket of the present invention and, due to this construction, even when an orthodontic treatment is started, there is eliminated any risk of the tip of the anterior tooth on the mandible being brought into contact with the bite plane BP of the bracket main body 31 attached to the lingual surface of the anterior tooth on the maxilla. This advantage over conventional brackets shown in FIGS. 2 and 3 becomes clear when the bite plane BP of the bracket of the present invention is compared with bite planes BP of the conventional brackets which are not as deep. Thus, according to the present invention, there is no risk of a gap being formed between lower and upper premolars or molars by virtue of the contact of the BP with the tip of the anterior tooth on the mandible. Thus, root resorption hardly occurs.

(3) Since the center point 29 of the LSW 27 generated when the LSW 27 is ligated in the slot 30 for fixation therein becomes close to the gingiva 26, there is no risk of the LSW 27 blocking the back of a substantially triangular gap, when viewed from the lingual side, formed between the two anterior teeth and the gingiva 26, and therefore even when food debris is lodged in the gap, it can easily be cleaned with a tooth brush or the like, and even a dental floss can be used for dental flossing without a risk of being blocked by the LSW 27, this facilitating oral cleaning.

(4) Since the main slot 30 opens toward the lingual surface 12 of the tooth 11 in a horizontal direction, when correcting the rotation of a tooth, the bracket may be ligated to the LSW 27 at a bracket having a wider span between brackets attached to adjacent teeth (inter bracket span), and therefore this facilitates ligating work and treatment of the rotated tooth when compared with the prior art bracket shown in FIG. 3 in which ligature has to be carried out at a narrower inter bracket span.

(5) Since the arm portion 33 of the bracket main body 31 extends relatively far so that it approaches the gingiva 26, a distance becomes quite large between the central axis of rotation of a tooth and the center point 29 of the LSW 27 residing in the main slot 30 and, as a result of this, the bracket of the present invention has an advantage over the conventional ones shown in FIGS. 2 and 3 in that even with smaller elasticity than those of the conventional bracket, a large magnitude of moment can easily be applied to a tooth needing a rotational correction. Therefore, a material having an elastic deformation more flexible than that of the conventional wire 17 can be used for the LSW 27.

(6) Since the main slot 30 opens in the horizontal direction toward the labial side, when compared with the conventional bracket 22 shown in FIG. 3 or the like, the LSW 27 in a shorter length can easily be installed in the main slot 30, whereby a tooth inclined inwardly of the remaining normal teeth can easily be pushed outwardly by virtue of the restoring force of the LSW 27 which tends to expand.

BRIEF DESCRIPTION OF THE DRAWINGS

FIG. 14 shows a configuration of a bracket suitable for use for an orthodontic appliance according to the present invention, in which (a) is a side view thereof and (b) is a plan view thereof with the pad omitted.

BEST MODE FOR CARRYING OUT THE INVENTION

Figure 11A:
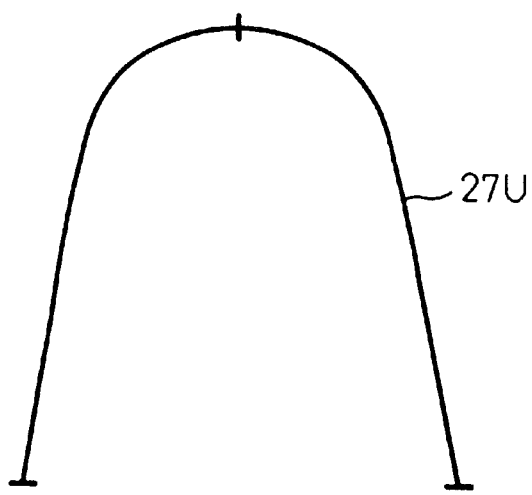
FIG. 11 is a plan view illustrating specific configurations, in which (a) shows a configuration for use for the maxilla, (b) shows a configuration for use for the mandible, and (c) shows a combination of the two.
Figure 11B:
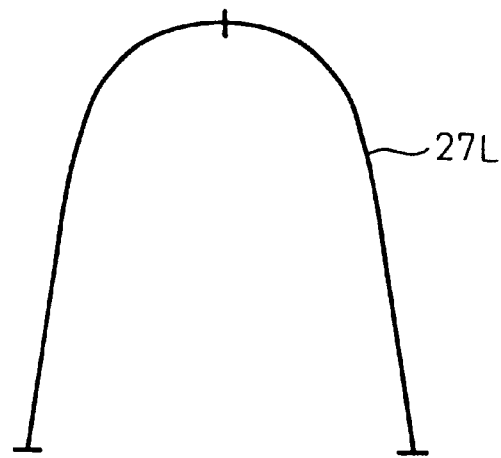
Figure 11C:
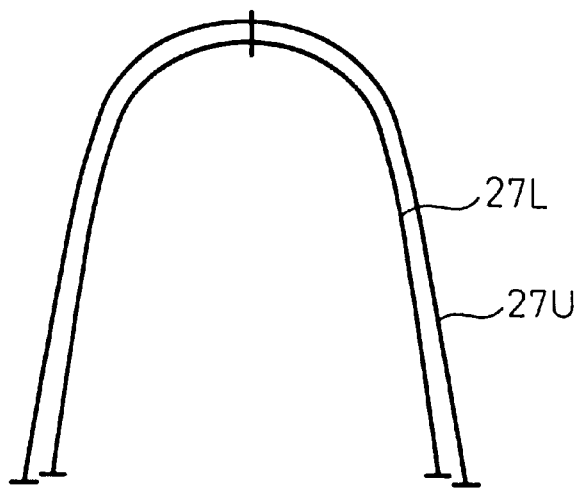

FIG. 11 illustrates a mode of operation of the present invention in which configurations as viewed from the top of LSW's (lingual straight archwires) 27 according to the present invention are shown. FIG. 11(a) shows an LSW 27U for use on a lingual surface of a maxilla, while FIG. 11(b) shows an LSW 27L for use on a lingual surface of a mandible. Each LSW 27 has a straight configuration comprising a simple smooth curve like an arc and straight lines continuously extending from ends of the curve without any difference in level. No bent portion through plastic deformation is formed at any position therealong, and each LSW rests on a horizontal plane as a whole in a state in which the LSW is not partially biassed for designed installation. In a state in which those LSW's are mounted on a tooth or teeth needing orthodontic treatment, both the LSW 27U and LSW 27L are partially deformed within the elastic limits thereof (within the ultra-elastic limits of a shape memory alloy when such an alloy is used for the wires), and they are inserted into a slot in a bracket, not shown, for ligature thereat, whereby they apply a corrective moment to a tooth via the bracket by virtue of a restoring force generated by the elasticity of thereof. In a state in which a needed orthodontic treatment is completed, the two LSW's 27 come to positions as shown in (c) where the respective teeth are biassed by them to be aligned on a proper dental arch.

Figure 12A:
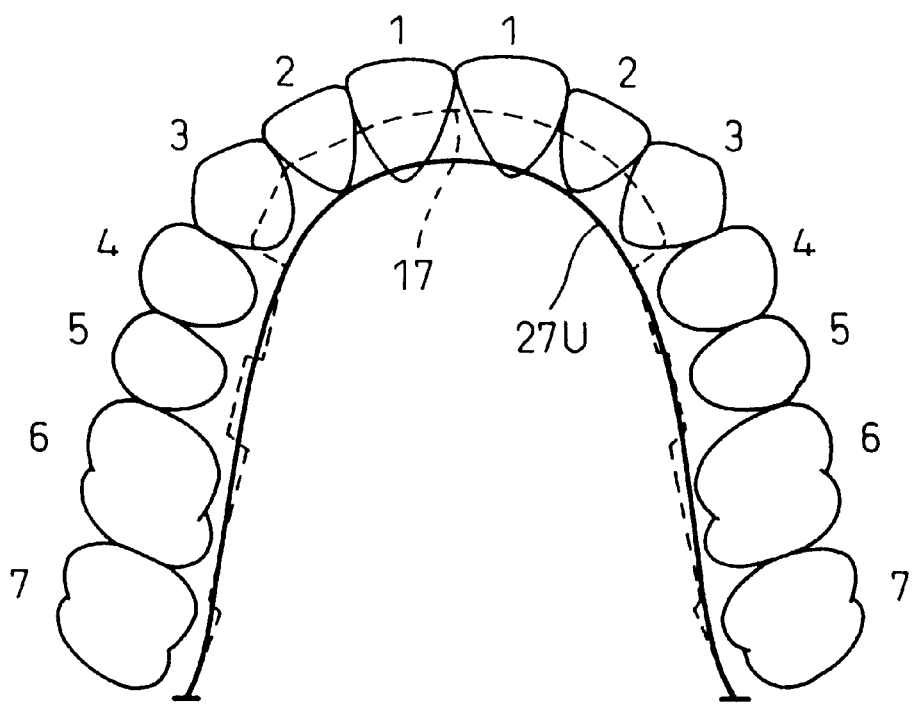
FIG. 12 is a plan view showing LSW's according to the present invention and conventional mushroom-shaped archwires for comparing their positions relative to a dental arch with no tooth extracted, in which (a) shows ones for use for the maxilla, while (b) shows ones for use for the mandible.
Figure 12B:
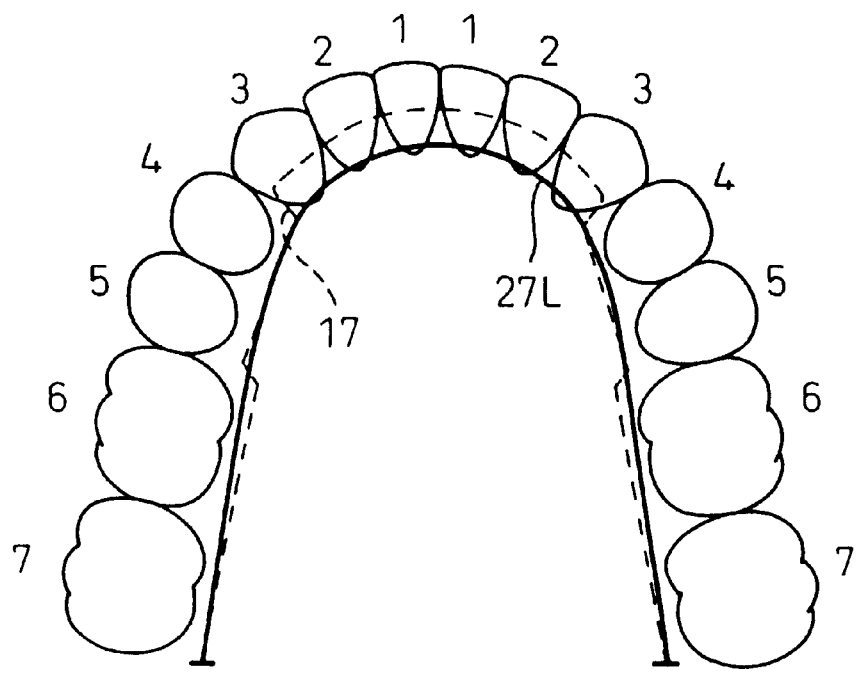
Figure 13A:
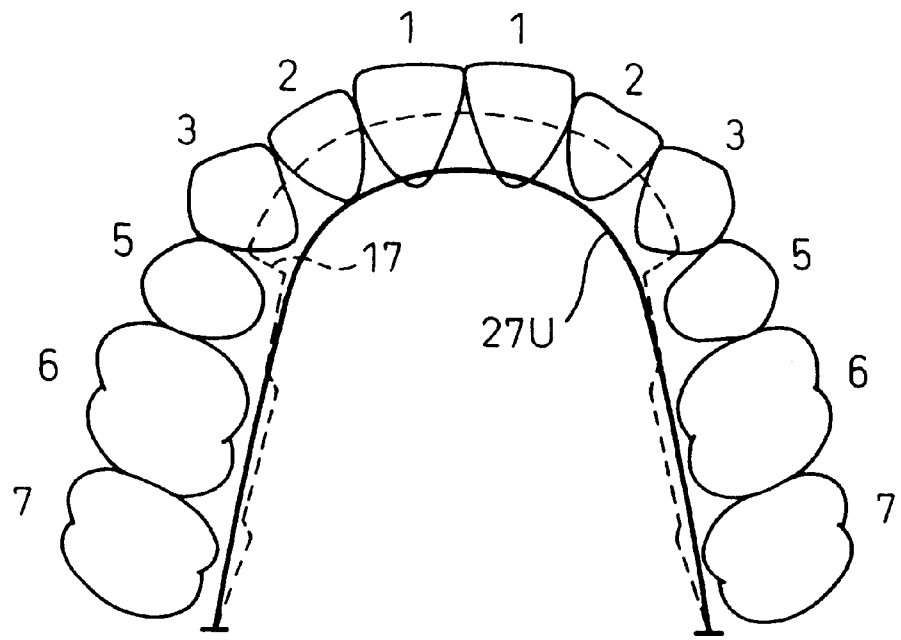
FIG. 13 is a plan view showing LSW's according to the present invention and conventional mushroom-shaped archwires for comparing their positions relative to a dental arch with extracted teeth, in which (a) shows ones for use for the maxilla, while (b) shows ones for use for the mandible.
Figure 13B:
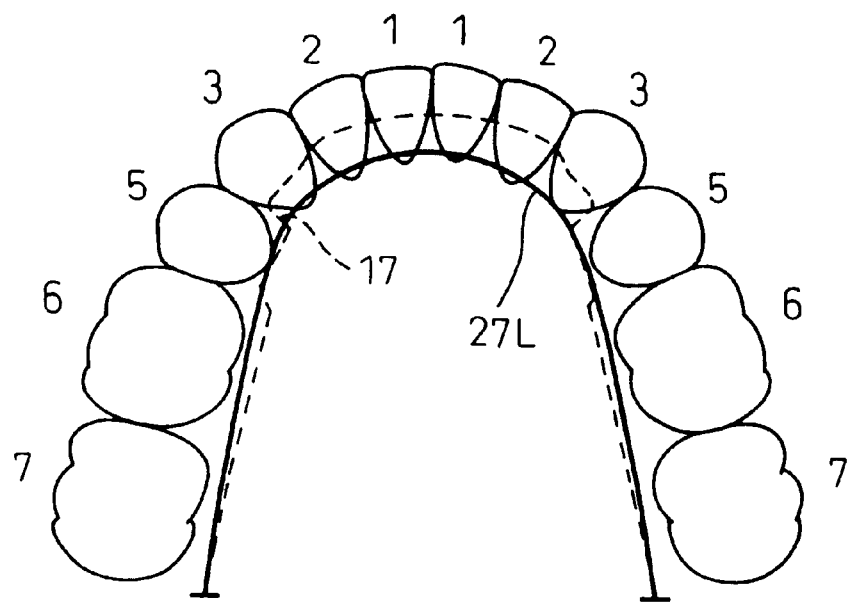

FIGS. 12 and 13 are plan views showing positions that the LSW's 27 take when the orthodontic treatment is completed. FIG. 12 shows a case in which the treatment needs no tooth extracted, with FIG. 12(a) showing a maxilla, and FIG. 12(b) showing a mandible. Conventional mushroom-shaped archwires 17 for the maxillary LSW 27U and mandibular LSW 27L, respectively, are shown in chained lines so as to clearly show differences in configuration and attachment position relative to the respective teeth between the LSW's 27 according to the present invention and the prior art wires 17. Similarly, FIG. 13 shows a case in which upper left and right first premolars and lower left and right first premolars are extracted to produce space needed for desired treatments, and similarly, (a) shows a maxilla, while (b) shows a mandible.

As is clear from FIGS. 12 and 13, the difference in configuration between the LSW 27 of the present invention and the conventional mushroom-shaped archwire 17 becomes most remarkable at a portion from a central incisor tooth 1 to a first premolar 4. Since the LSW 27 of the present invention passes uniformly from the front to the rear through the same horizontal plane along the lingual surface of the gingiva rather than the lingual surface of the teeth at a relatively low position on the respective teeth which is close to the aforesaid LP (lingual point), even at an anterior teeth portion where anterior teeth (1 to 3) on the maxilla and mandible are overlapped when viewed in a horizontal direction, tips of the mandibular teeth hardly come into contact with the LSW 27 on the maxillary teeth. In addition, for the same reason, not only can a gap between adjacent teeth be cleaned by brushing so as to remove food debris lodged therein but also the gap can be flossed.

Since there is provided no plastically deformed bent portion on the LSW 27 of the present invention, production of LSW's can be facilitated and an industrial mass production thereof can be attained, therefore providing tremendous advantages in that the production cost is reduced and that ready-made LSW's 27 can be used as they are. In addition, even in a case where the position of the LSW 27 has to be changed for adjustment by causing the LSW 27 to slide relative to the bracket as an orthodontic treatment progresses, since no troublesome work inherent in the prior art mushroom-shaped archwire 17 is needed which includes re-bending of bent portions and re-ligating of the adjusted archwire, the sliding adjustment of the wire can be facilitated in a very simple fashion, thus alleviating loads borne by both an orthodontist and a patient and reducing a gap in technique between individual orthodontists. Moreover, since basically there is no need to form bent potions on the LSW 27 to conform with dental arches of individual patients, although an ultra-elastic deformation is available with the LSW 27 of the present invention in a more flexible way than with the prior art wire 17, there is also provided another tremendous advantage in that a shape memory alloy of Ni, Ti, Cu or the like can be used which is hard to plastically deform so as to provide a bent portion.

Next, FIG. 14 illustrates a configuration and a construction which are specific to the bracket 28 suitable for use together with the LSW 27 in the orthodontic appliance according to the present invention. As briefly shown in FIG. 1 and described previously, the bracket main body 31 of the bracket 28 is made integral by a method such as using brazing with the pad 13 attached to the lingual surface of a tooth by a method such as bonding. As indicated by 34a, 34b, 34c in FIG. 14, a brazing surface 34 of the bracket main body is formed by cutting an end portion of the bracket main body 31 depending on the position of a corresponding position on the LSW 27, and the position and degree of inclination of the lingual surface of a tooth to which the bracket 28 is attached, whereby a distance between the pad 13 and the LSW 27 is compensated for by the length of the arm portion 33 of the bracket main body 31, thereby making it possible to support the LSW 27 on the same horizontal plane in a state in which the dental arch is proper even if the lingual surface of a tooth is inclined. Moreover, in bonding the pad 13 to the lingual surface of a tooth, if there are indentations in the surface of the tooth, they can be filled with an adhesive or the angle of the pad 13 relative to the surface of the tooth can be finely adjusted with an adhesive.

The main slot 30 is formed in the bracket main body 31 substantially horizontally, and an opening 35 is formed in such a manner that it opens toward the pad 13, and hence the lingual surface of a tooth to which the bracket is attached, in other words, toward the labial direction. This facilitates an operation of installing the LSW 27 into the main slot 30 to a great extent, whereby in so installing the LSW 27, deflection and ligature of the LSW 27 with a thin wire can also be facilitated. In addition, a sub-slot 36 is formed in the bracket main body 31 so that a thin wire or rubber band can securely be hooked therein for ligating the LSW 27 to the main slot 30.

Figure 1:
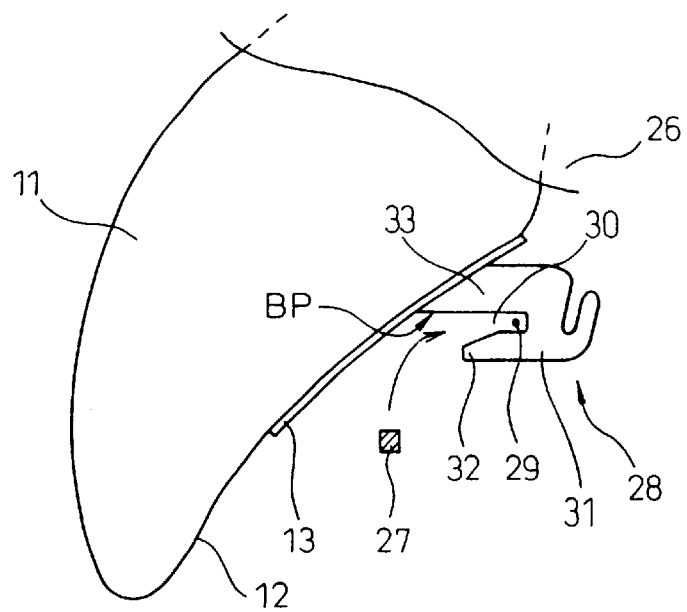
FIG. 1 is a side view briefly showing a mode of operation of the present invention.
Figure 2:
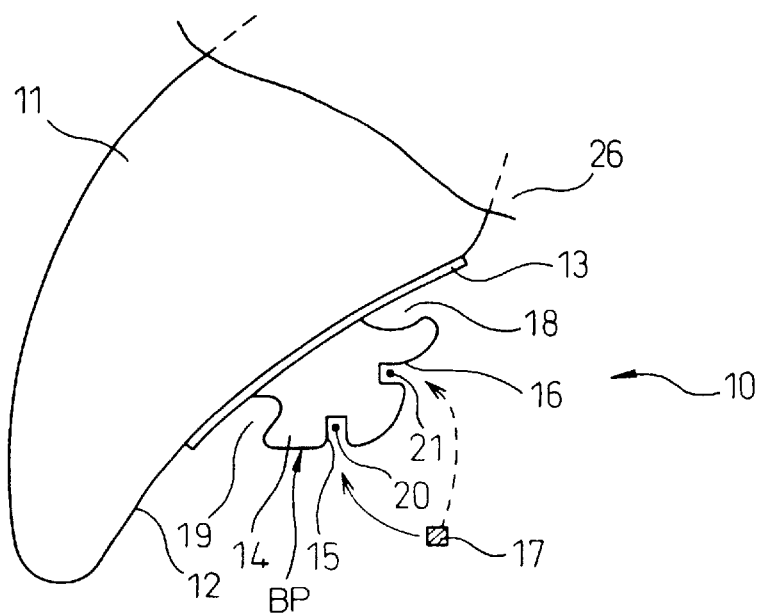
FIG. 2 is a side view showing a first conventional example.

In the bracket 28, the opening 35 of the main slot 30 opens toward the lingual surface of the teeth, and the tip of the leg portion 32 of the bracket main body 31 forms a relatively large space 37 between the pad 13 and the tip itself, and therefore even when the bracket 28 is attached, as shown in FIG. 1, to the anterior tooth 11 of the maxilla so as to confront the tip of an anterior tooth on the mandible, since the bite plane BP is formed under the lower surface of the arm portion 33 of the bracket main body 31, the position of the BP is deepened, whereby the tip of the anterior tooth on the mandible hardly collides with the BP. Therefore, there is no risk of a gap being formed between the upper and lower premolars and molars by virtue of collision of the BP with the tip of the anterior tooth on the mandible, a risk of a root resorption being generated at the anterior tooth being thereby eliminated.

In addition, as described before, the main slot 31 opens toward the lingual surface 12 of the tooth 11 in a horizontal direction and, therefore, in correcting the rotation of a tooth, the bracket may be ligated to the LSW 27 at a portion where a wider inter bracket span can be provided, thus facilitating the ligating operation. Moreover, since the arm portion 33 is extended relatively far so as to approach the gingiva 26 at the anterior teeth 1 to 3, even if the elasticity of the LSW 27 is small, a large moment can be obtained for correction of the rotation of a tooth.

Figure 15:
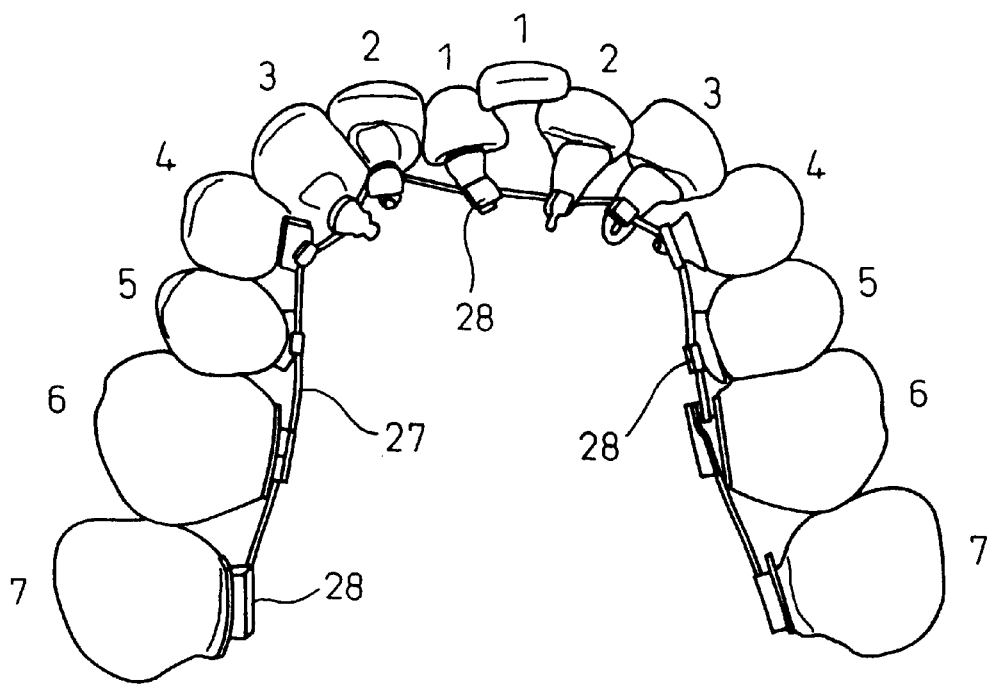
FIG. 15 is a plan view illustrating an orthodontic appliance according to the present invention when an orthodontic treatment is started.

In starting an orthodontic treatment, brackets 28 to be used are selected and adopted from ready-made brackets in conformance with teeth to be corrected, pads 13 for the selected brackets 28 are bonded to the lingual surfaces of respective teeth 1 to 3, so that center points 29 of the respective main slots 30 come to reside on a position on the aforesaid horizontal LSP (lingual straight plane) which should be taken by the LSW27 in a state in which the orthodontic treatment is completed. Then, the LSW 27 is deflected within the elastic deformation range thereof and is then hooked in the respective slots 30, whereupon the LSW 27 is ligated to the slots with a thin wire or rubber band for fixation therein. A state is illustrated in FIG. 15 in which the LSW 27 is hooked in a way as described above for initiation of an orthodontic treatment.

As shown in FIG. 11, the LSW 27 is a smooth straight wire having no bent portion and comprising a simple curve and straight lines continuously following ends of the curve without a difference in level. However, the position and direction of the slot 30 becomes random due to the position or rotation of a tooth to be corrected, and therefore when it is ligated within the slot 30, the LSW 27 deflects within the elastic limit thereof as described before, whereby it deforms into an irregular shape as shown in FIG. 15, a force or rotational moment being thereby applied to the bracket which acts to correct the displaced position or rotation of the tooth. In addition, like the central incisor tooth 1 on the right-hand side of the mandible shown in FIG. 15, it will not be a problem even if there is a tooth having no LSW 27 hooked thereon because attachment of a bracket 28 thereto is difficult at the time of initiation of an orthodontic treatment. This is because after there is formed a sufficient space as the treatment progresses, a bracket 28 may be attached to the tooth, so that the LSW 27 can be hooked the bracket 28 so attached.

Figure 16:
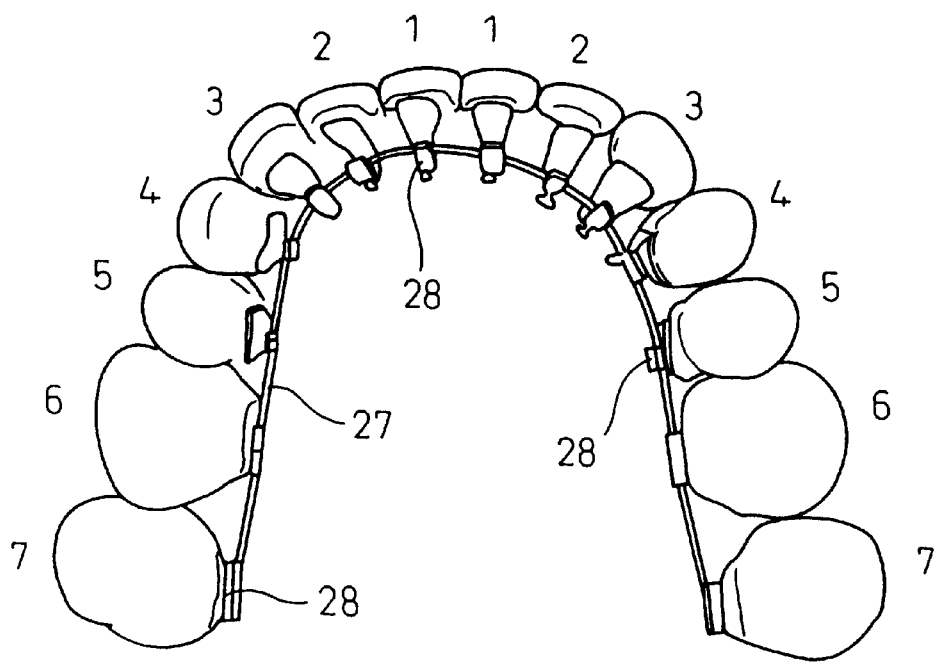
FIG. 16 is a plan view illustrating an orthodontic appliance according to the present invention when an orthodontic treatment is completed.

Since the position of the LSW 27 relative to the bracket is displaced as the treatment progresses, the LSW 27 needs to be caused to slide relative to the bracket 28 for adjustment. Since there is no bent portion formed on the LSW 27 through plastic deformation, the LSW 27 can be caused to freely slide relative to the slot in the bracket 28. FIG. 16 shows a state in which the orthodontic treatment is completed. In such a state, the respective teeth 1 to 7 come to normal positions, and the LSW 27 also restores a configuration close to its intrinsic smooth configuration.

Figure 3:
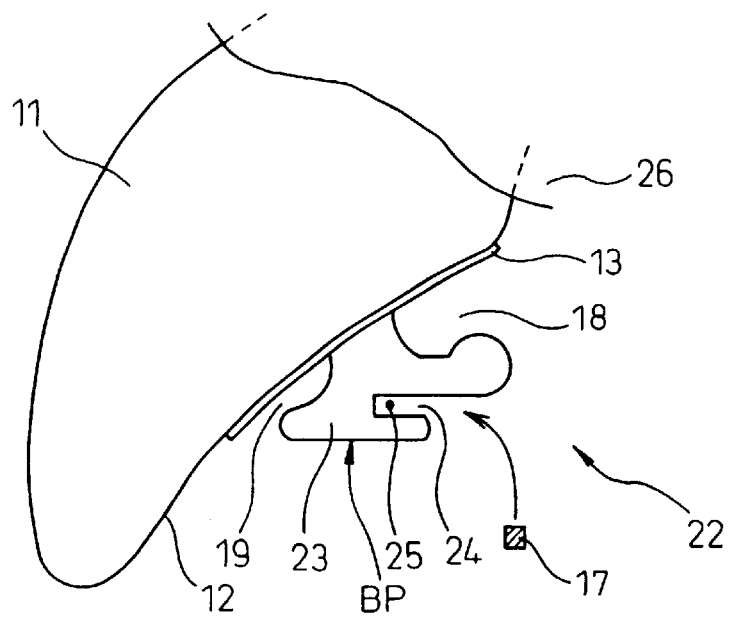
FIG. 3 is a side view showing a second conventional example.
Figure 4:
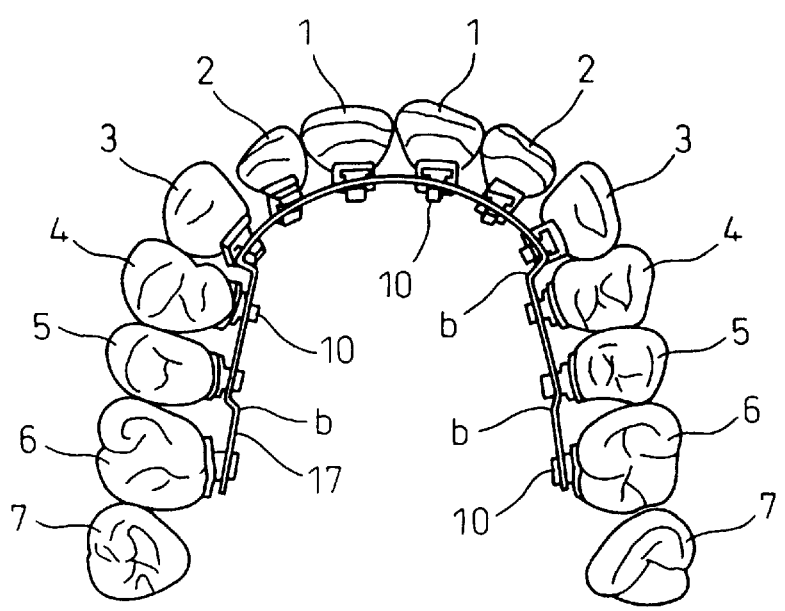
FIG. 4 is a plan view showing the conventional example as a whole.
Figure 5:
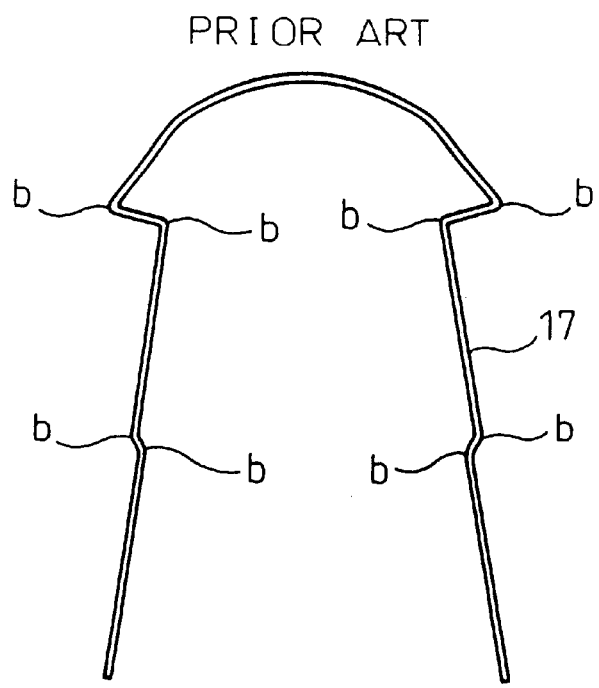
FIG. 5 is a plan view illustrating a conventional mushroom-shaped archwire.
Figure 6:
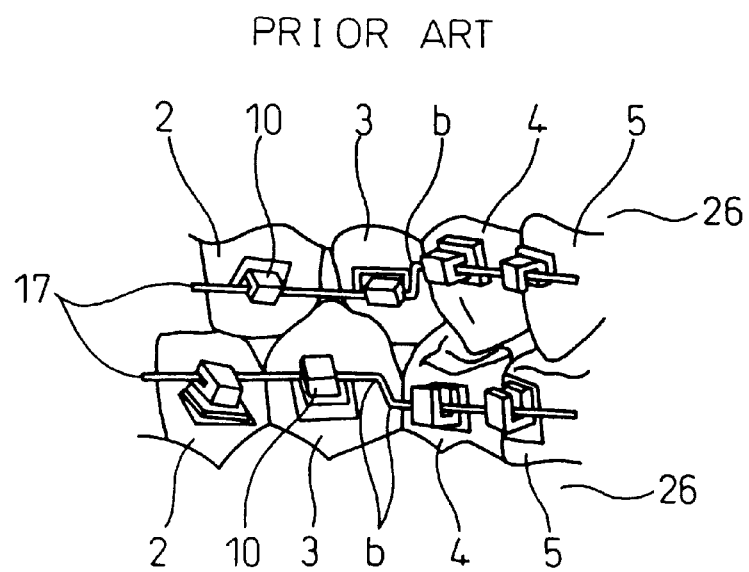
FIG. 6 is a front view of the conventional example as viewed from the lingual side of the teeth.
Figure 7:
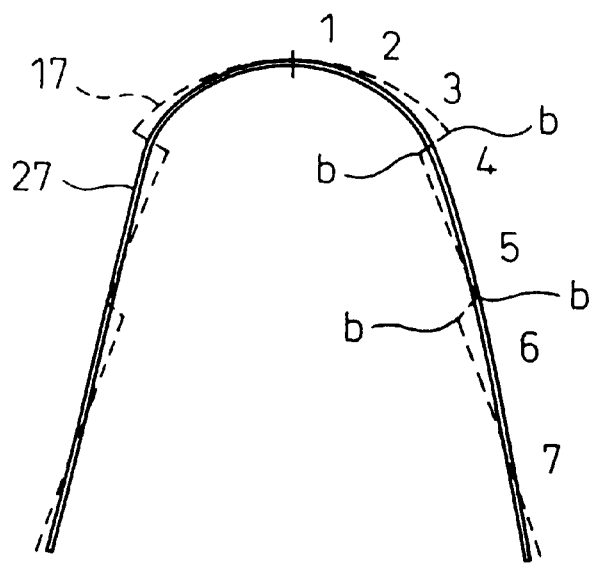
FIG. 7 is a plan view showing a specific example of a lingual straight archwire (LSW) according to the present invention and the conventional mushroom-shaped archwire together for comparison therebetween.
Figure 8:
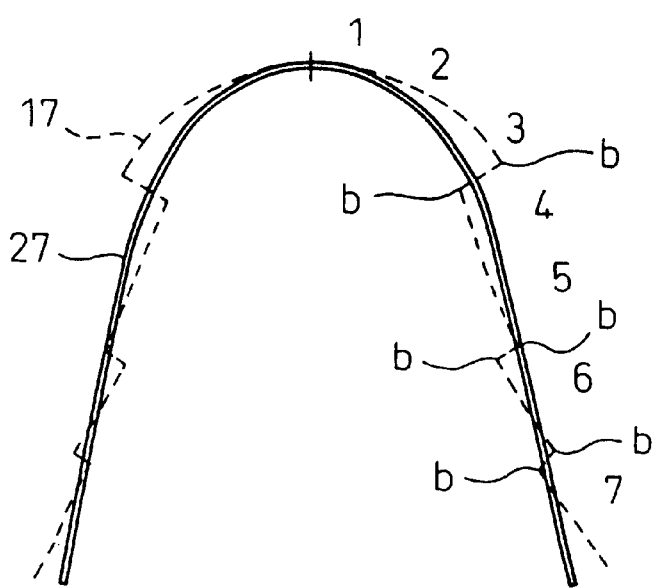
FIG. 8 is a plan view showing another specific example of the LSW according to the present invention and another example of the conventional mushroom-shaped archwire together for comparison therebetween.
Figures 9A, 9B, 9C:
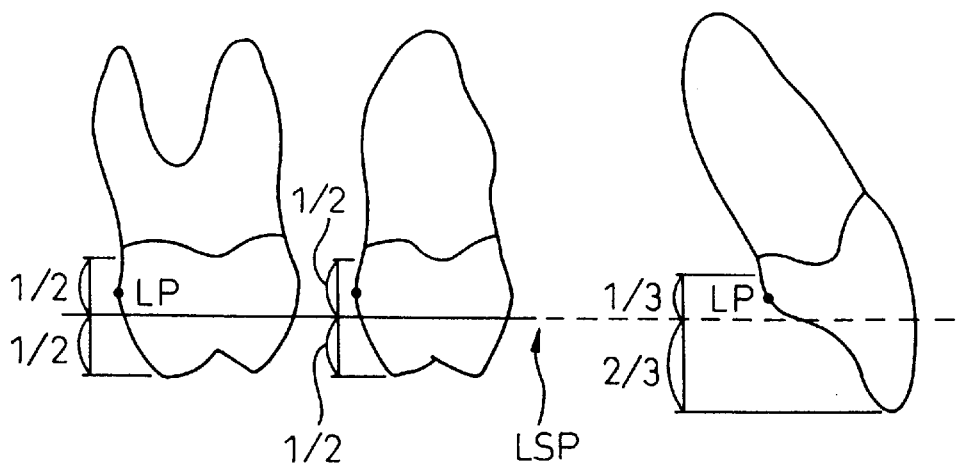
FIG. 9 is a side view of teeth for explaining an idea on which the present invention is based.
Figure 10:
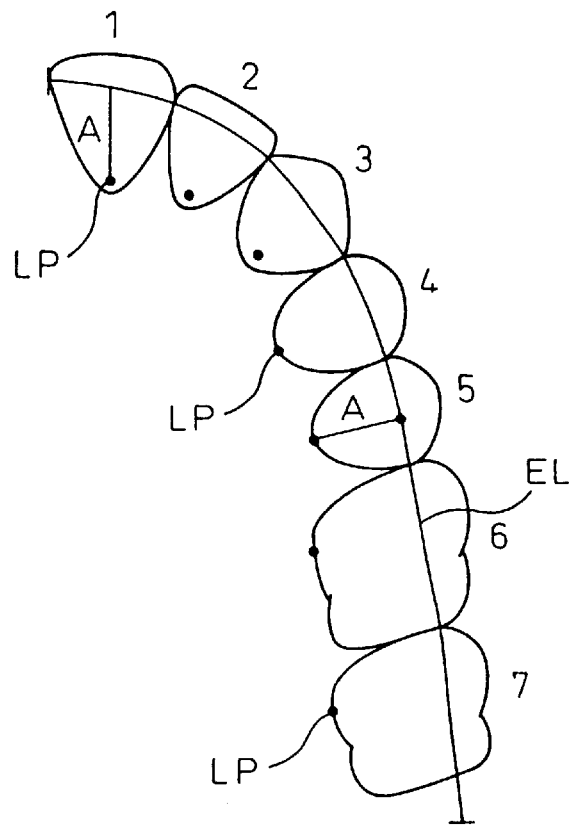
FIG. 10 is a plan view showing a dental arch e for explaining an idea on which the present invention is based.
Figure 17:
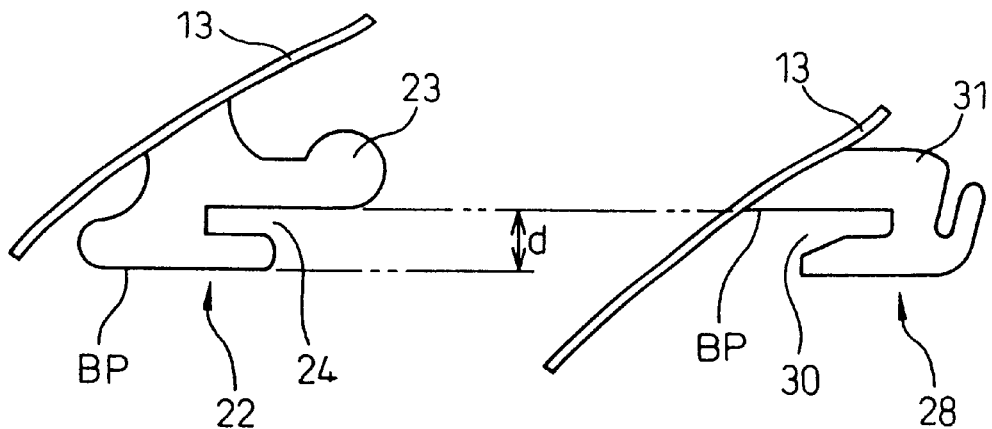
FIG. 17 is a side view illustrating an advantage of the bracket according to the present invention over the conventional bracket through comparison therebetween.

FIG. 17 illustrates the above-described advantage of the bracket 28 of the present invention shown in FIGS. 1 and 14, and the prior art bracket 22 shown in FIG. 3 is also shown therein for the purpose of comparison with the bracket of the present invention for clear understanding of the advantage. When comparing cases where the bracket main body 31 the bracket 28 of the present invention and the bracket main body 23 of the conventional bracket 22 are assumed to be brazed to the same pad 13 which is bonded to the lingual surface of the same tooth, it is found that even if the main slots 24, 30 of the respective bracket main bodies 22, 31 are formed at the same height, there exists a large difference in height indicated by (d) between the bite planes of the respective bracket main bodies which each face the tip of a corresponding tooth. It is clear from FIG. 17 that with the bracket 28 according to the present invention being used on an anterior tooth, there is an extremely reduced possibility that the bracket 28 comes into collision with the mating tooth.

FIGS. 18 to 21 illustrate the results of experimental orthodontic treatments carried out using the orthodontic appliance according to the present invent in which specific values are disclosed which were obtained for respective portions when the corrective treatment was completed. Namely, an orthodontic treatment is started with a view to attaining as an anticipated target states shown in the drawings. In addition, values A shown on tables in the drawings each denote a distance from the Embrasure Line by Andrews (EL) to the lingual point LP of the respective teeth, and values B denote a distance from the LP of the respective teeth to the lingual straight archwire LSW 27 which passes through a position very close to the LP. In addition, values C denote a value equal to A+B, in other words, a distance from the EL to the LSW 27. The unit for use for numeric values shown on the drawings and tables is millimeter.

Figure 18:
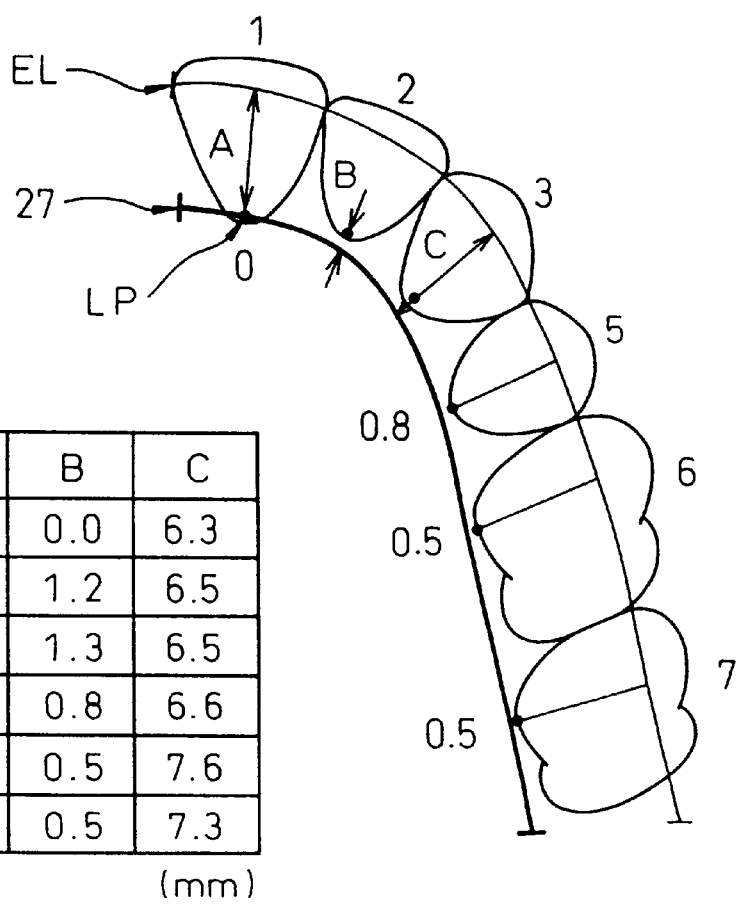
FIG. 18 is a plan view illustrating reference points (LP) and wire positions on a maxillary dental arch with an extracted tooth which are actually used to determine the configuration of an LSW according to the present invention.

First of all, FIG. 18 illustrates the state of the maxillary teeth 1 to 7 when an orthodontic treatment was carried out relative to the maxillary dental arch after the first premolars 4 had been extracted as is often carried out in such a treatment. As is clear from FIG. 18, in this case, in total, six points were set as a passing point through which the straight LSW 27 should pass which rests on the horizontal LSP (lingual straight plane) and comprises a simple and smooth curve and straight lines connected to ends of the curve without a difference in level, the points being, as viewed in a vertical direction, the LP's (lingual point) of the left and right central incisors and points 0.5 mm spaced inwardly away from the LP's of the left and right first and second molars 6 and 7. In this case, as a result of such setting, although there were produced a distance B of about 1.2 mm between the LP of the lateral incisor 2 and the LSW 27 and a distance B of about 0.8 mm between the LP of the second premolar 5 and the LSW 27, distances to those extents posed no problem.

Figure 19:
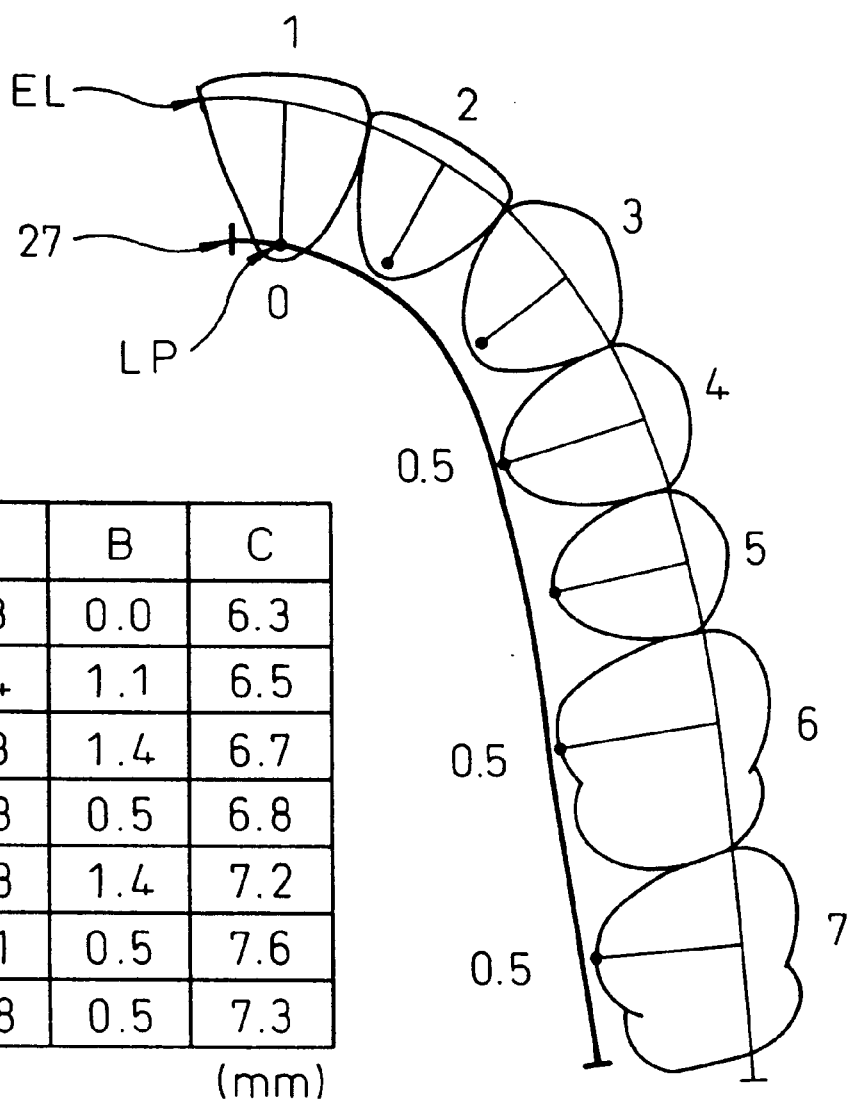
FIG. 19 is a plan view illustrating reference points (LP) and wire positions on a maxillary dental arch with no extracted tooth which are actually used to determine the configuration of an LSW according to the present invention.

FIG. 19 illustrates the state of the maxillary teeth 1 to 7 when an orthodontic treatment was carried out with no tooth extracted. In this case, in total, eight points were set as a point through which the LSW 27 should pass; in other words, in addition to six points similar to those set in the case shown in FIG. 18, another two points were set about 0.5 mm lingually away from the LP of the left and right first premolar 4. Thus, the LSW 27 prepared for this experimental treatment was given a configuration which allows it to pass through those eight points.

Figure 20:
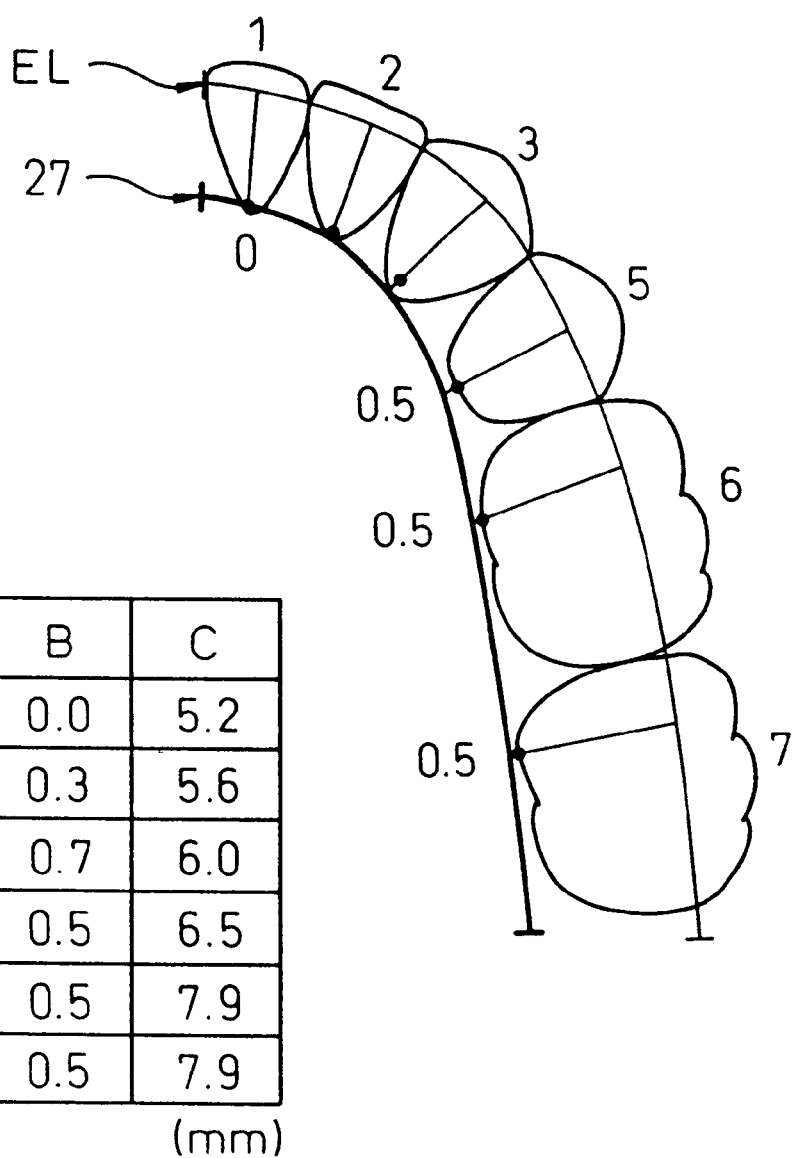
FIG. 20 is a plan view illustrating reference points (LP) and wire positions on a mandible dental arch with an extracted tooth which are actually used to determine the configuration of an LSW according to the present invention.
Figure 21:
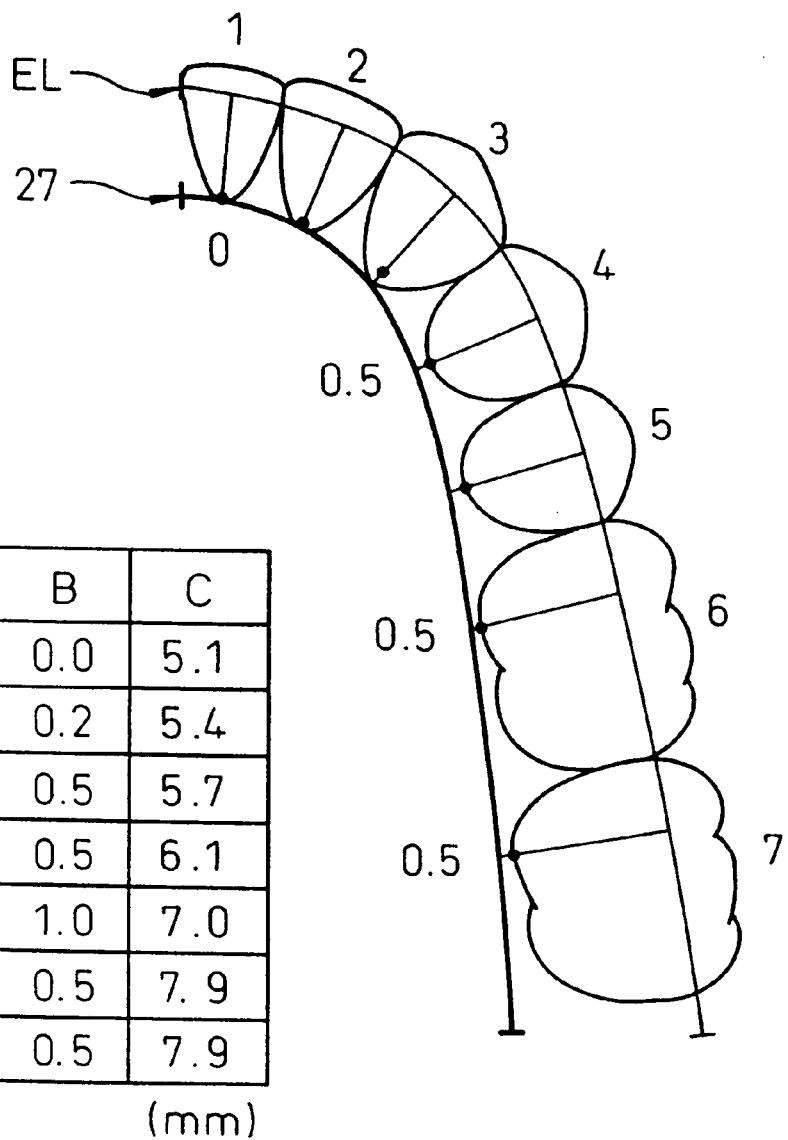
FIG. 21 is a plan view illustrating reference points (LP) and wire positions on a mandible dental arch with no extracted tooth which are actually used to determine the configuration of an LSW according to the present invention.

Similarly, FIGS. 20 and 21 illustrate embodiments carried out with respect to the mandible, in which FIG. 20 shows the state of the mandibular teeth which received the orthodontic treatment after the left and right first premolars 4 had been extracted, while FIG. 21 shows the state of the mandibular teeth which received an orthodontic treatment with no tooth extracted. In either case, eight points were set as a reference point for determination of a configuration for the LSW 27, the points being the LP's of the central incisor teeth 1 and points about 0.5 mm spaced lingually away from the LP's of the first molar 6 and the second molar 7. In addition thereto, in the case shown in FIG. 20, more points were set about 0.5 mm lingually away from the second premolars 5, and in the case shown in FIG. 21, more points were set about 0.5 mm lingually away from the LP's of the respective first premolars 4. Thus, in either case, in total, eight points were set as a reference point for determination of the configuration of the LSW 27. Since these were the cases with the mandible, when looking at the teeth alignment in a transverse direction, there are found few irregularities along the lingual surfaces of the respective teeth, and thus the values B are not more than abut 1 mm.

Figure 22A:
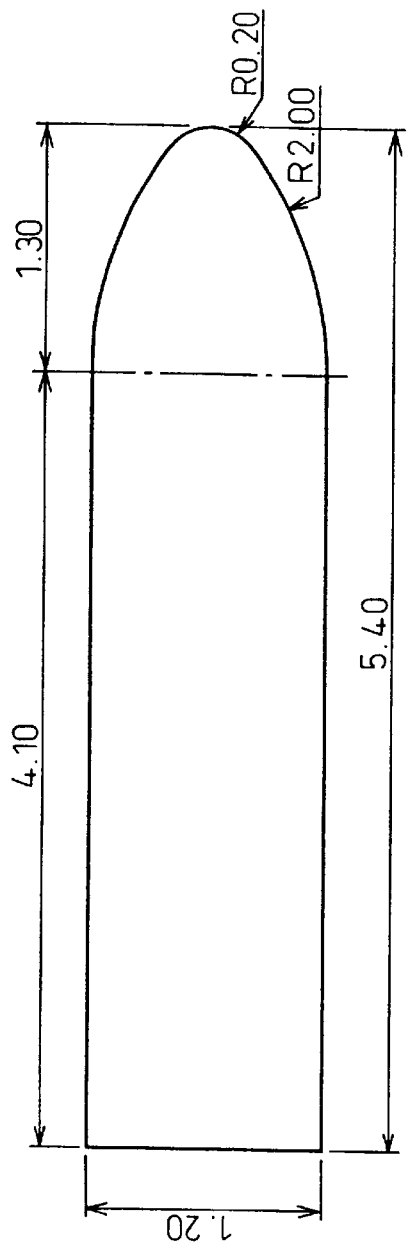
FIG. 22 illustrates specific configuration and dimensions of a bracket main body according to the present invention, in which (a) is a plan view of the bracket main body and (b) is a side view thereof.
Figure 22B:
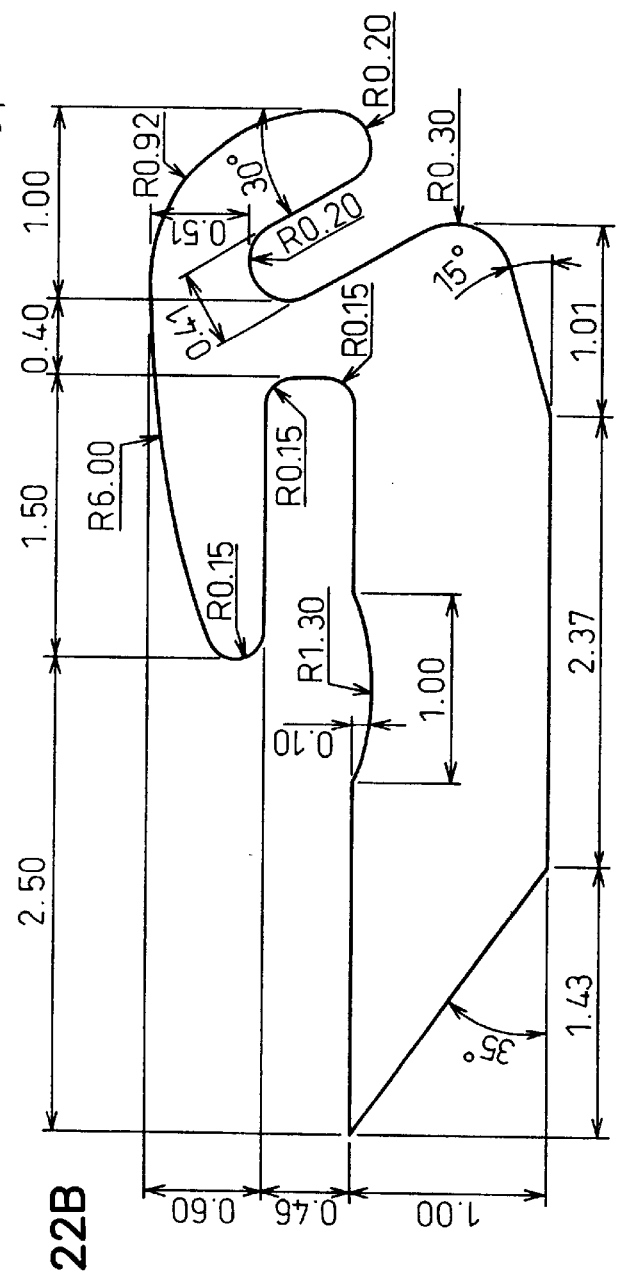

FIG. 22 illustrates an embodiment of a bracket main body 31 of the bracket 28 as described using FIG. 14 before including a configuration and dimensions which are specific to the bracket main body, which bracket main body is suitable for constituting the orthodontic appliance according to the present invention together with the LSW (lingual straight archwire) 27. Millimeters are the units used for the figures indicated therein except for angles. In addition, R denotes a radius curvature in mm. It is needless to say that in carrying out the present invention, the configuration and figures shown in FIG. 22 may be altered to some extent.

What is claimed is:

1. An orthodontic appliance configured for installation on a patient's teeth, the orthodontic appliance comprising:

a wire having no sharply bent portion either in a vertical direction or in a horizontal direction and being smoothly curved in a horizontal plane, where the horizontal plane passes through anterior teeth and through positions situated as high as about one-half height of a crown on a lingual side of molars, wherein said wire follows in proximity to and along an envelope defined by protruding apexes of lingual surfaces of the patient's teeth in a desired aligned position; and a plurality of brackets, each bracket adapted to be attached to the lingual surface of a tooth patient's teeth so as to connect the wire to the lingual surfaces of the patient's teeth, each bracket having a main slot with an opening toward said tooth when said appliance is installed on said patient's teeth, said main slot for receiving said wire.

2. The orthodontic appliance as set forth in claim 1 wherein:

the horizontal plane passes through positions situated as high as about one-third the height of a crown on the lingual side of the anterior teeth where said orthodontic appliance is configured for use on a maxilla; and the horizontal plane passes through positions situated as high as about one-half the height of a crown on the lingual side of the anterior teeth where the orthodontic appliance is configured for use on a mandible.

3. The orthodontic appliance as set forth in claim 1, wherein:

said wire passes in proximity to apexes of lingual surfaces of central incisor teeth, where the lingual surfaces of the central incisor teeth expand from the necks thereof in such a manner as to protrude lingually; and said wire passes in proximity to points about 0.5 mm lingually away from apexes of the lingual surfaces of crowns of first premolars, first molars and second molars.

4. The orthodontic appliance as set forth in claim 3, wherein said wire passes through points about 0.8 mm lingually away from apexes of the lingual surfaces of crowns of second premolars where the first premolars are extracted from the patient's teeth.

5. The orthodontic appliance as set forth in claim 1 wherein each bracket comprises:

a pad adapted to be attached to the lingual surface of the tooth; and a bracket main body adapted to be made integral with said pad, said bracket main body having formed therein an arm portion having a length needed to connect said wire to the lingual surfaces of said respective teeth, said arm portion being made integral with a back of said pad after the position of a cut end at one end thereof and angle thereof are adjusted, said main slot being formed in said arm portion at the other end thereof.

6. A bracket of an orthodontic appliance configured for installation on a patient's tooth, said bracket comprising:

a pad adapted to be attached to lingual surface of the tooth; and a bracket main body adapted to be made integral with said pad, said bracket main body having formed therein an arm portion having a length needed to connect a wire to the lingual surfaces of the patient's teeth and a slot for attachment of the wire therein, said arm portion being made integral with a back of said pad after the position of a cut end at one end thereof and an angle thereof are adjusted, said slot being formed in said arm portion at the other end thereof which opens toward the lingual surface of the tooth for accommodation and ligature of the wire, said slot having an opening toward said pad, said main body also having a sub-slot for ligating the wire to the slot.

7. The bracket for an orthodontic appliance as set forth in claim 6, wherein the direction of said slot is set such that it becomes substantially horizontal when said bracket is attached to the lingual surface of each tooth.

8. The bracket for an orthodontic appliance as set forth in claim 6, wherein said pad is attached to the lingual surface of the tooth by bonding with an adhesive, and the degree of filling of said adhesive is regulated such that the position of said slot is finely adjusted so as to match a wire to be received by said slot with a desired position.

* * * * *